(12) United States Patent
Stahl et al.

(10) Patent No.: US 7,154,004 B2
(45) Date of Patent: Dec. 26, 2006

(54) CATALYTIC TRANSAMIDATION AND AMIDE METATHESIS UNDER MODERATE CONDITIONS

(75) Inventors: Shannon S. Stahl, Madison, WI (US); Samuel H. Gellman, Madison, WI (US); Sarah E. Eldred, Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 18 days.

(21) Appl. No.: 10/785,301

(22) Filed: Feb. 24, 2004

(65) Prior Publication Data

US 2004/0230078 A1    Nov. 18, 2004

Related U.S. Application Data

(60) Provisional application No. 60/449,975, filed on Feb. 24, 2003.

(51) Int. Cl.
    *C07C 233/05*    (2006.01)
(52) U.S. Cl. .................................................... 564/219
(58) Field of Classification Search ............... 564/219
    See application file for complete search history.

(56) References Cited

U.S. PATENT DOCUMENTS

| | | | |
|---|---|---|---|
| 4,018,747 A | 4/1977 | Malz et al. | |
| 5,302,756 A | 4/1994 | McKinney | |
| 5,395,974 A | 3/1995 | McKinney | |
| 5,587,498 A * | 12/1996 | Krogh et al. | .................. 554/69 |
| 6,281,307 B1 * | 8/2001 | Muhlebach et al. | ........ 526/171 |

FOREIGN PATENT DOCUMENTS

WO    WO 03/020797 A1    3/2003

OTHER PUBLICATIONS

Kondo et al, Tetrahedron, vol. 56, 8883-8891, 2000.*
Bon et al., (1994) "Aluminum Chloride-Promoted Transamidation Reactions," *J. Org. Chem.* 59:4035-4036.

* cited by examiner

*Primary Examiner*—Shailendra Kumar
(74) *Attorney, Agent, or Firm*—Joseph T. Leone, Esq.; DeWitt Ross & Stevens S.C.

(57) ABSTRACT

Disclosed is a method of manipulating the carboxamide functionality in a catalytic manner. The method includes the steps of reacting amides with or without amines in the presence of various types of metal catalysts, at a temperature of about 250° C. or less.

18 Claims, 6 Drawing Sheets

FIG. 1

| | Amine | Catalyst | % Yield[b] |
|---|---|---|---|
| 1 | PhCH₂NH₂ | Sc(OTf)₃ | 97 |
| | | Ti(NMe₂)₄ | 99 (80) |
| 2 | CH₂=CHCH₂NH₂ | Sc(OTf)₃ | 98 (79) |
| | | Ti(NMe₂)₄ | 88 |
| 3 | iBuCH₂NH₂ | Sc(OTf)₃ | 68 |
| | | Ti(NMe₂)₄ | 98 (84[c]) |
| 4 | MeOCH₂CH₂NH₂ | Sc(OTf)₃ | 99 (98) |
| | | Ti(NMe₂)₄ | 2 |

FIG. 2

| | R | R' | Catalyst | Amide Ratio (I/II)[b] | |
|---|---|---|---|---|---|
| | | | | Forward | Reverse |
| 1 | PhCH$_2$– | CH$_2$=CHCH$_2$– | Sc(OTf)$_3$ | 89/11 | 6/94 |
| | | | Ti(NMe$_2$)$_4$ | 92/8 | 5/95 |
| | | | Al$_2$(NMe$_2$)$_6$ | 50/50 | 49/51 |
| 2 | PhCH$_2$– | iPrCH$_2$– | Al$_2$(NMe$_2$)$_6$ | 46/54 | 44/56 |
| 3 | iBuCH$_2$– | CH$_2$=CHCH$_2$– | Al$_2$(NMe$_2$)$_6$ | 57/43 | 55/45 |

| | X | X' | Catalyst | Amide Ratio (III/IV)[b] | |
|---|---|---|---|---|---|
| | | | | Forward | Reverse |
| 1 | H | CH$_3$ | Sc(OTf)$_3$ | 98/2 | 1/99 |
| | | | Ti(NMe$_2$)$_4$ | 42/58 | 42/58 |
| | | | Al$_2$(NMe$_2$)$_6$ | 65/35 | 43/57 |
| 2 | H | CH$_3$O | Ti(NMe$_2$)$_4$ | 34/66 | 32/68 |
| 3 | CH$_3$ | CH$_3$O | Ti(NMe$_2$)$_4$ | 40/60 | 41/59 |

CATALYTIC TRANSAMIDATION AND AMIDE METATHESIS UNDER MODERATE CONDITIONS

CROSS-REFERENCE TO RELATED APPLICATIONS

Priority is claimed to provisional application Ser. No. 60/449,975, filed Feb. 24, 2003, the contents of which are incorporated herein.

FEDERAL FUNDING

This invention was made with United States government support awarded by the following agency: NSF 9820952. The United States has certain rights in this invention.

FIELD OF THE INVENTION

The invention relates to a method of manipulating carboxamide-containing molecules via low-temperature transamidation and amide metathesis reactions using a specified class of catalysts. The invention encompasses both low-temperature transamidation between or among amine and amide reactants, as well as low-temperature amide metathesis reactions between or among amide reactants, in the presence of a metal catalyst. The disclosed reaction functions at greatly reduced temperatures and pressures as compared to conventional transamidation reactions. Thus, the invention is useful because it saves energy and related costs when fabricating and manipulating amide-containing molecules and makes possible amide metathesis as a method for fabricating and manipulating carboxamide-containing molecules and polymers.

BACKGROUND OF THE INVENTION

Transamidation and amide metathesis represent novel means of producing polyamides and small carboxamide-containing molecules. These reactions are attractive from the design perspective because their starting materials, amides and amines, can be easily obtained with highly diverse functionalities. An important aspect of using transamidation or amide metathesis to synthesize polyamides and small molecules is the production of new, highly-stable molecules with useful properties. Further, the most stable component of a random mixture of molecules can be selected and amplified using the principles of dynamic covalent chemistry (DCC). (For reviews, see Sanders et al. (2002) "Dynamic Covalent Chemistry," *Angew. Chemie Intl. Edn.*, 41:898.) In amide-based DCC, alternative amide linkages equilibrate with one another, thereby giving rise to novel products. In short, in a dynamic combinatorial library of amides or amines, all compounds are in thermodynamic equilibrium, allowing the library composition to adapt to external influences. Thus, for example, binding forces between a ligand and its receptor can be used to select, stabilize and, thereby amplify the best amide-containing or amine-containing inhibitor in the library. In this scenario, ligand-induced amplification can be used to identify amide- or amine-containing inhibitors of important receptors.

There are several examples of transamidation currently in the literature. Descriptions of these methods can be found, for example, in U.S. Pat. No. 4,018,747 to Malz et al., U.S. Pat. No. 5,395,974 to McKinney, and U.S. Pat. No. 5,302,756 to McKinney, each of which is incorporated herein. While the reactions described in these patents provide methods to manipulate polyamides, the reactions all suffer from certain shortcomings. These shortcomings include the high levels of ammonia used to drive the reaction, reaction temperatures exceeding 300° C., and reaction pressures well above atmospheric pressure. Also, none of these patents describe the manipulation of small organic molecules, nor do they involve amide metathesis.

Consequently, there is an unmet need for a method that allows the manipulation of polyamides, as well as small carboxamide-containing molecules, which does not suffer from these shortcomings. There is also a need for a method capable of producing carboxamide-containing molecules and polyamide compounds of suitable quality for experimental research and commercial production.

SUMMARY OF THE INVENTION

It is therefore a primary object of the invention to provide a method of producing amides, oligoamides, and polyamides comprising a low-temperature transamidation reaction between amines and amides, or an amide metathesis reaction between or among amides.

It has been found that by using an appropriate catalyst, both transamidation and amide metathesis reactions can be induced at temperatures far lower than currently described. These reactions comprise the exchange of amide and amine functionalities in the case of transamidation reactions, and the exchange of amide functionalities in the case of amide metathesis reactions. This reactivity results in the synthesis of new amide-based molecules.

Thus, the preferred embodiments of the invention are: (1) a low-temperature transamidation reaction wherein an amine-amide reactant pair is reacted; and (2) a low-temperature amide metathesis reaction wherein two or more distinct amides are reacted. Both of these reactions take place in a non-polar, aprotic solvent, in the presence of a metal-containing catalyst, at a temperature of about 250° C. or less.

The reaction disclosed herein will readily take place at about 250° C. or less, and even at about 150° C. or less. The preferred temperature range for the reaction is from about 90° C. to about 250° C.

The preferred metal-containing catalysts for use in the method are transition metal-amido complexes, main group metal-amido complexes, Lewis acids, and combinations thereof. From among these, the preferred catalysts are aluminum-, lanthanum-, scandium-, tantalum-, tin-, titanium-, ytterbium-yttrium-, and zirconium-containing catalysts. The most preferred catalysts for use in the invention are $Sc(OTf)_3$, $Ti(NMe_2)_4$ and $Al_2(NMe_2)_6$.

The preferred solvent is an aromatic, non-polar, aprotic solvent, such as toluene.

The invention is also directed to a method fabricating combinatorial libraries comprising amide-containing and/or amine-containing molecules. The method comprises reacting in a solvent a plurality of reactants, the reactants being at least two distinct amides, or a plurality of at least one amide and at least one amine. The reaction takes place in the presence of a metal-containing catalyst, and at a temperature of about 250° C. or less. Under these conditions, a reaction selected from the group consisting of transamidation and amide metathesis reactions takes place.

BRIEF DESCRIPTION OF THE FIGURES

[a]Reaction conditions: Amine (0.83 mmol), N-phenyl heptanamide (0.3 mmol), catalyst (0.017 mmol), 2 mL toluene, 90° C., 16 h.

[b]GC yields (internal standard=triphenylmethane); isolated yield in parentheses from scaled-up reactions (2 to 5 mmol).

[c]Yield based on $^1$H-NMR integration of the isolated amide mixture.

[a]Reaction conditions: Amine (0.33 mmol), amide (0.33 mmol), catalyst (0.017 mmol), 2 mL toluene, 90° C., 20 h.

[b]Determined by GC (internal standard=triphenylmethane) and $^1$H NMR. The starting materials and products shown are the only species observed by these methods.

[a]Reaction conditions: Amine (0.33 mmol), Amide (0.33 mmol), Catalyst (0.033 mmol), 2 mL p-xylene, 120° C., 20 h.

[b]Determined by GC (Internal Standard=tripehnyl methane). The starting materials and products shown are the only species observed.

DETAILED DESCRIPTION OF THE INVENTION

Metal-catalyzed transamidation (eq. 1) has very little precedent. Transamidation can be achieved at high temperatures (>250° C.) with amide polymers or polymer/amine mixtures; reported conditions sometimes include Lewis acid promoters. Bertrand and coworkers demonstrated that stoichiometric $AlCl_3$ mediates transamidation between carboxamide-amine (eq 1)

R = Alkyl, R' = Aryl: [cat] = $Sc(OTf)_3$ or $Ti(NMe_2)_4$
R = Alkyl, R' = Alkyl: [cat] = $Al_2(NMe_2)_6$
R = Aryl, R' = Aryl: [cat] = $Ti(NMe_2)_4$ pairs at 90° C. See Eric Bon, Dennis C. H. Bigg, and Guy Bertrand (1994) "Aluminum Chloride-Promoted Transamidation Reactions," *J. Org. Chem.* 59:4035–4036. Identifying efficient catalysts for this important transformation would significantly expand the exploration and utility of transamidation.

With this concept in mind, the present invention was conceived such that the above transamidation reaction can now be run in a catalytic fashion. Three classes of transamidation catalysts were initially selected for evaluation: (1) Lewis acidic metal complexes; (2) nucleophilic alkali-metal amidos; and (3) transition-metal and main-group amidos.

EXAMPLE 1

The following metal complexes were tested for catalytic activity. Each is commercially available from national and international suppliers (e.g., Aldrich Chemicals, Milwaukee, Wis.; Sigma Chemicals, Milwaukee, Wis.):

(a) tetrakis(dimethylamido)titanium(IV) {$Ti(NMe_2)_4$}
(b) tetrakis(dimethylamido)zirconium(IV) {$Zr(NMe_2)_4$}
(c) pentakis(dimethylarmido)tantalum(V) {$Ta(NMe_2)_5$}
(d) lithium(bis(trimethylsilyl)amido) {$Li(NTMS)$}
(e) sodium(bis(trimethylsilyl)amido) {$Na(NTMS_2)$}
(f) potassium(bis(trimethylsilyl) amido) {$K(NTMS_2)$}
(g) bis(bis(trimethylsilyl)amido)zinc(II) {$Zn(NTMS_2)_2$}
(h) tris(bis(trimethylsilyl)amido)yttrium(III) {$Y(NTMS_2)_3$}
(i) tris(bis(trimethylsilyl)amido)lanthanum(III) {$La(NTMS_2)_3$}
(j) bis(bis(trimethylsilyl)amido)tin(II) {$Sn(NTMS_2)_2$}
(k) tetrakis (diethylamido)tin(IV) {$Sn(NEt_2)_4$}
(l) scandium tris(trifluorumethanesulfonate) {$Sc(OTf)_3$}
(m) yttrium tris(trifluoromethanesulfonate) {$Y(OTf)_3$}
(n) lanthanum tris(trifluoromethanesulfonate) {$La(OTf)_3$}
(o) ytterbium tris(trifluoromethanesulfonate) {$Yb(OTf)_3$}
(p) lithium tetrakis(dimethylamido)aluminate {$LiAl(NMe_2)_4$}
(q) tris(dimethylamido)aluminum(III) dimer {$Al2(NMe_2)_6$}
(r) aluminum trichloride {$AlCl_3$}.

Figure 1:
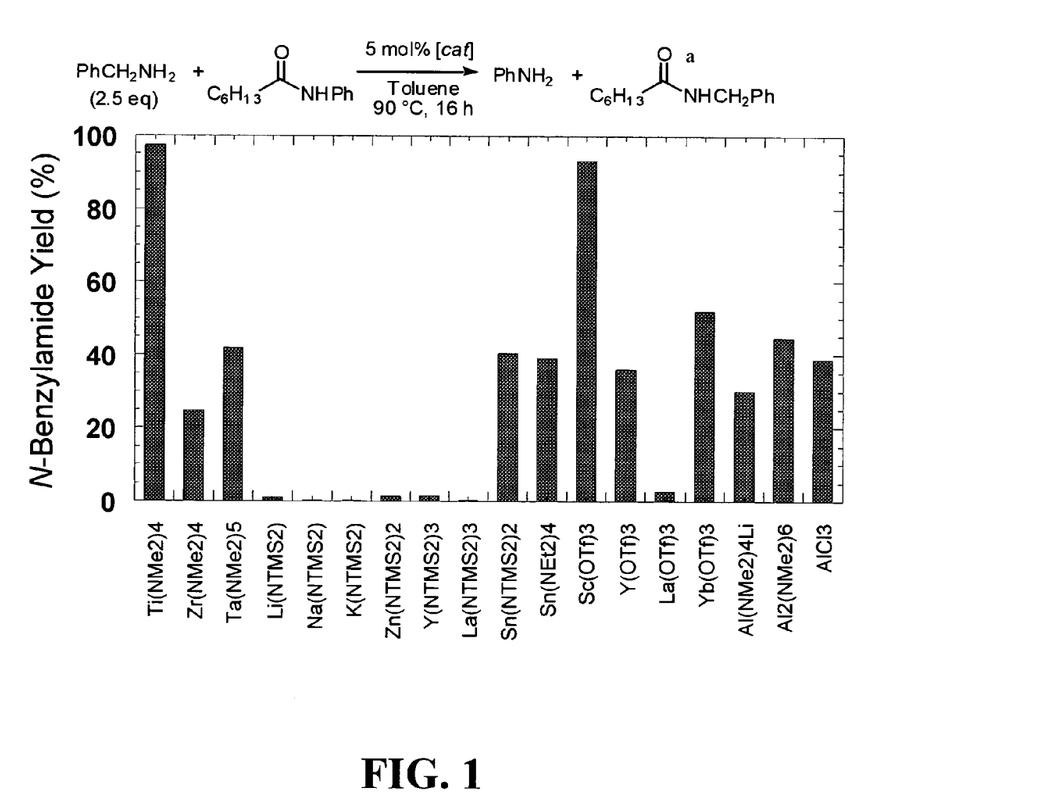
FIG. 1 is a graph depicting the catalyst screening results for the exchange of benzyl amine and the N-phenyl heptanamide starting material. Yields are based on the average of duplicate runs. All catalysts are present at 5% loading with respect to the N-phenyl amide. $Al_2(NMe_2)_6$ loading is calculated based on monomeric $Al_2(NMe_2)_3$.
Figure 2:
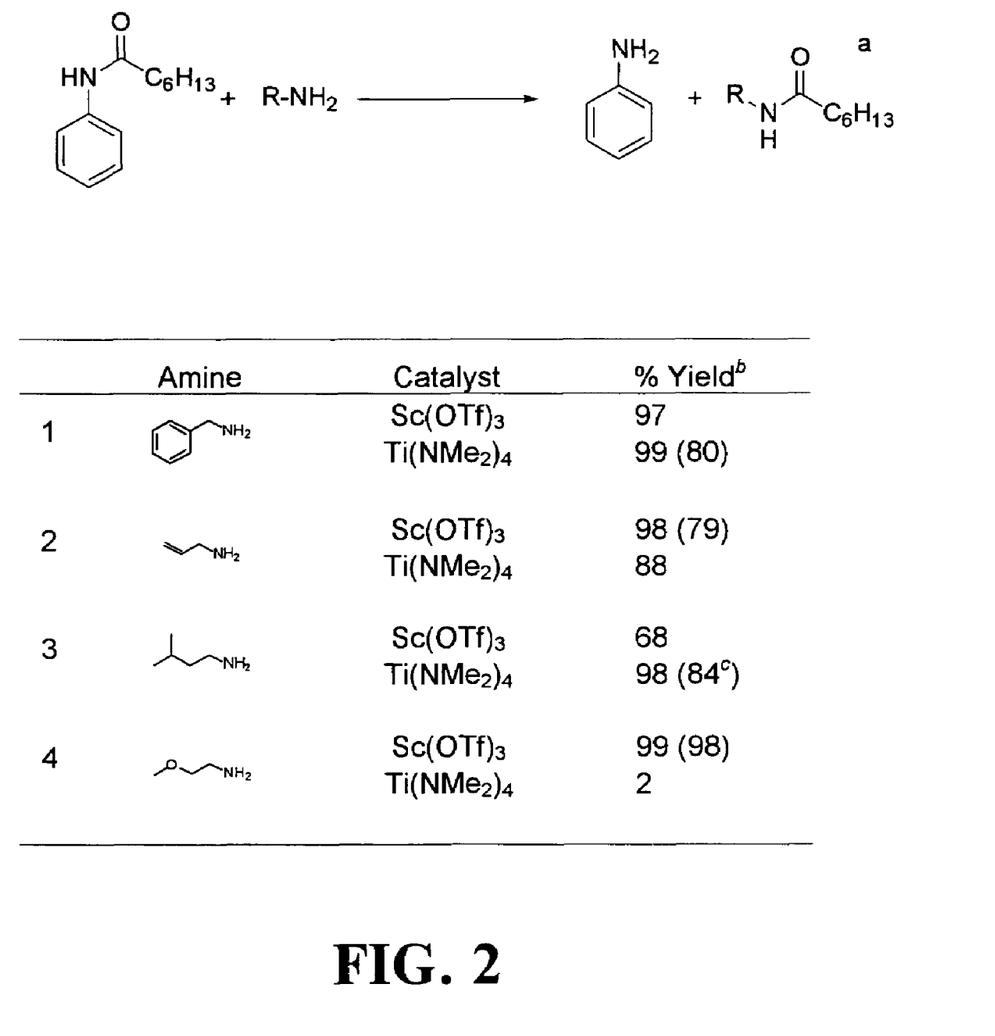
FIG. 2 is a table detailing the transamidation of N-phenyl heptanamide with primary alkyl amines and correlating the catalyst species with the percent yield.

Each of these compounds was tested at 5 mol % loading for its ability to promote transamidation starting from benzyl amine and N-phenyl heptanamide (see FIG. 1). This reaction is thermodynamically favored in the direction shown because of destabilizing cross-conjugation in the N-phenyl amide. In the absence of a catalyst, however, this reaction proceeds only very slowly. Specifically, in the absence of a catalyst, after a one-month reaction period at 90° C., only 39% conversion was observed in the background reaction between benzyl amine and N-phenyl heptanamide. In contrast, and as shown in FIG. 1, many of the metal complexes listed above catalyzed the transamidation reaction between benzyl amine and N-phenyl heptanamide after only 16 hours of reaction time at 90° C. in toluene. Several of the metal complexes from among those tested promoted significant reaction within 16 hours at 90° C. (see FIG. 1). Most notably, $Ti(NMe_2)_4$ and $Sc(OTf)_3$ (OTf=trifluoromethane sulfonate) promoted near quantitative conversion to the N-benzyl heptanamide product. Three other alkyl amines (allylamine (2), isopentyl amine (3), and methyloxyethylamine (4)) displayed similar reactivity with these two catalysts (see FIG. 2). Thus, in the preferred embodiment, the reaction is carried out in a non-polar, aprotic solvent (and most preferably in an aromatic, aprotic solvent).

EXAMPLE 2

Figure 3:
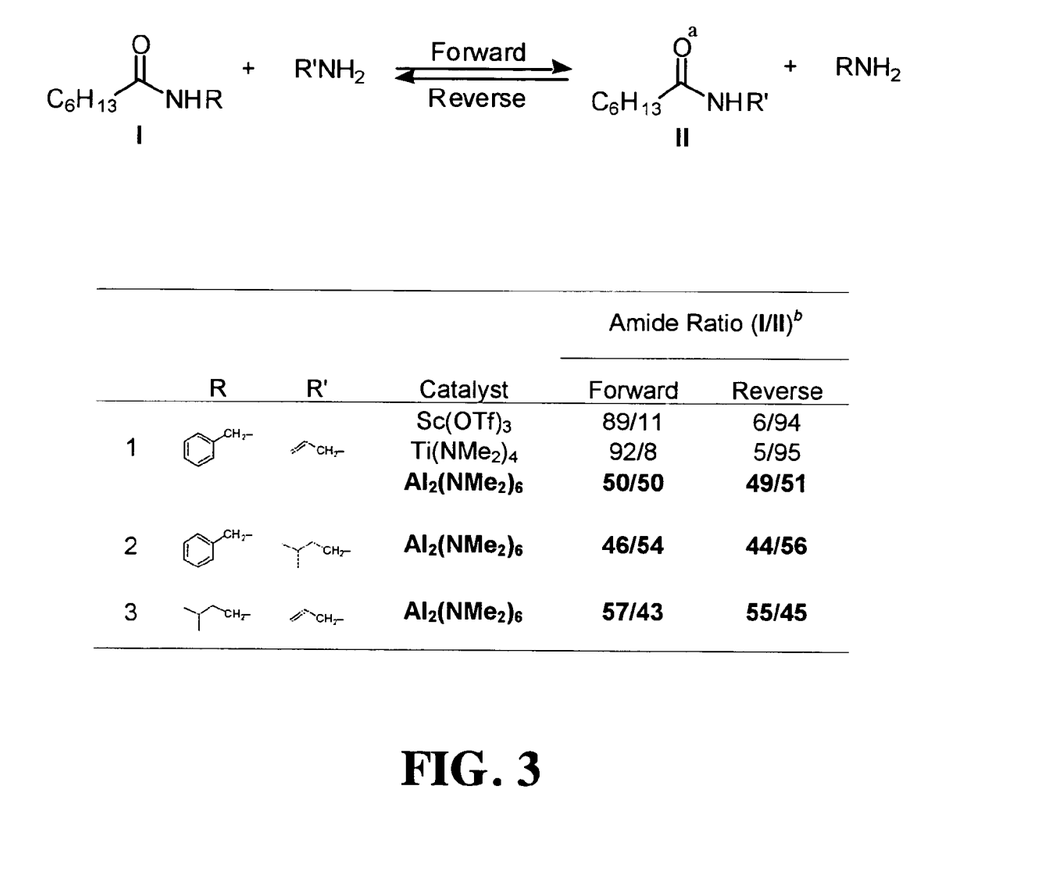
FIG. 3 is a table illustrating the results of catalytic transamidation reactions of N-alkyl heptanamide with primary alkyl amines.

To investigate catalytic transamidation in the absence of an intrinsic thermodynamic driving force, exchange reactions between alkyl amines and N-alkyl amides, which are approximately thermoneutral, were examined. Three alkyl amine/N-alkyl amide pairs were selected, and their equilibration was studied at a 1:1 substrate ratio (see FIG. 3). These substrates exhibit essentially no reaction in the absence of a catalyst, even after heating at 90° C. for one month.

Figure 4:
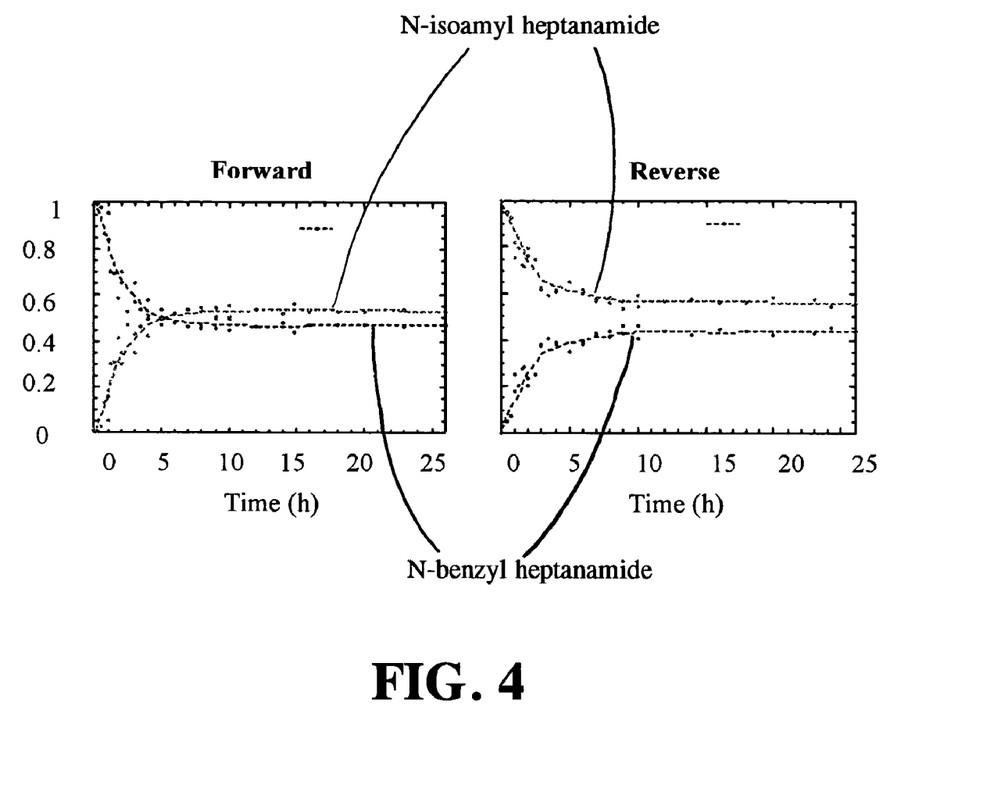
FIG. 4 represents time course data for the $Al_2(NMe_2)_6$-catalyzed equilibrium exchange between N-benzyl heptanamide/isoamyl amine, forward, and N-isoamyl heptanamide/benzyl amine, reverse.

Equilibration reactions in the presence of a catalyst were conducted starting from each side of the reaction for each amine/amide pair. The scandium and titanium catalysts, successful in the reactions with the N-aryl amide (see FIGS. 1 and 2), functioned, but only poorly, with the N-alkyl amide substrates (see FIG. 3). In contrast, the dimeric aluminum complex $Al_2(NMe_2)_6$ consistently exhibited good reactivity. Nearly identical amide ratios were obtained when the reactions were carried out in either direction (see FIGS. 3 and 4). Thus, each of the $Al_2(NMe_2)_6$-catalyzed transamidation reactions appears to have reached equilibrium within 20 hours at 90° C.

EXAMPLE 3

Figure 5:
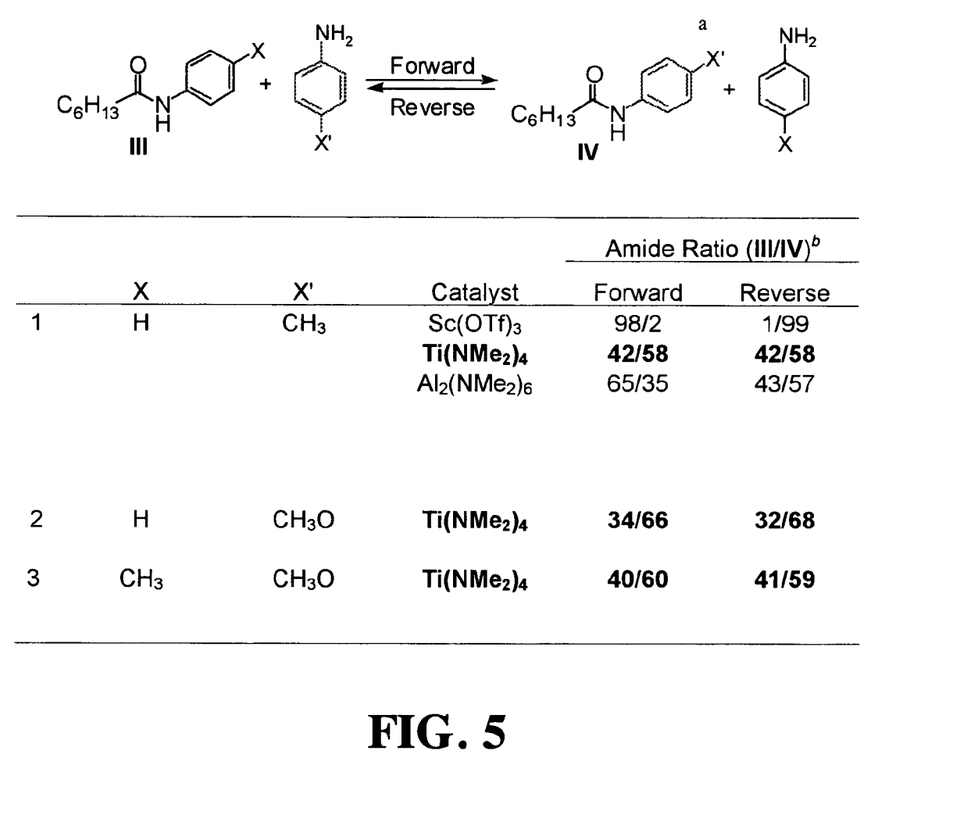
FIG. 5 is a table similar to that shown in FIG. 3 for the case of transamidation between aryl amines and aryl amides.

One of the most important aspects of this chemistry is that equilibrium can be reached between starting material and product amines and amides. Three aryl amine/N-aryl amide pairs were selected, and their equilibration was studied at a 1:1 substrate ratio (see FIG. 5). Equilibrium transamidation can also be achieved between anilines and N-aryl amides, although somewhat more forcing conditions are required for this reaction than for the analogous reaction involving alkyl amines and alkyl amides (see FIG. 5). These substrate/product pairings are approximately thermoneutral, similar to the alkyl/alkyl pairings.

Equilibration reactions in the presence of a catalyst were conducted in both directions for each amine/amide pair. Both of the metal amido complexes $Ti(NMe_2)_4$ and $Al_2(NMe_2)_6$ display activity; however, in this case, the titanium catalyst is more effective. Nearly identical amide ratios were obtained when the reactions were carried out in either direction (see FIG. 5). Thus, each of the $Al_2(NMe_2)_6$-catalyzed transamidation reactions appears to have reached equilibrium within 20 hours at 120° C.

The results outlined in Examples 1, 2, and 3 provide the first demonstration of metal-catalyzed transamidation under moderate conditions. These findings represent an important prerequisite for dynamic covalent chemistry and template-directed synthesis of carboxamides. The disclosed method constitutes an important step in the elucidation of these mechanistic principles and constitutes an important step in the synthesis and formation of new polyamide species and carboxamide-containing small molecules with novel properties.

EXAMPLE 4

Figure 6:
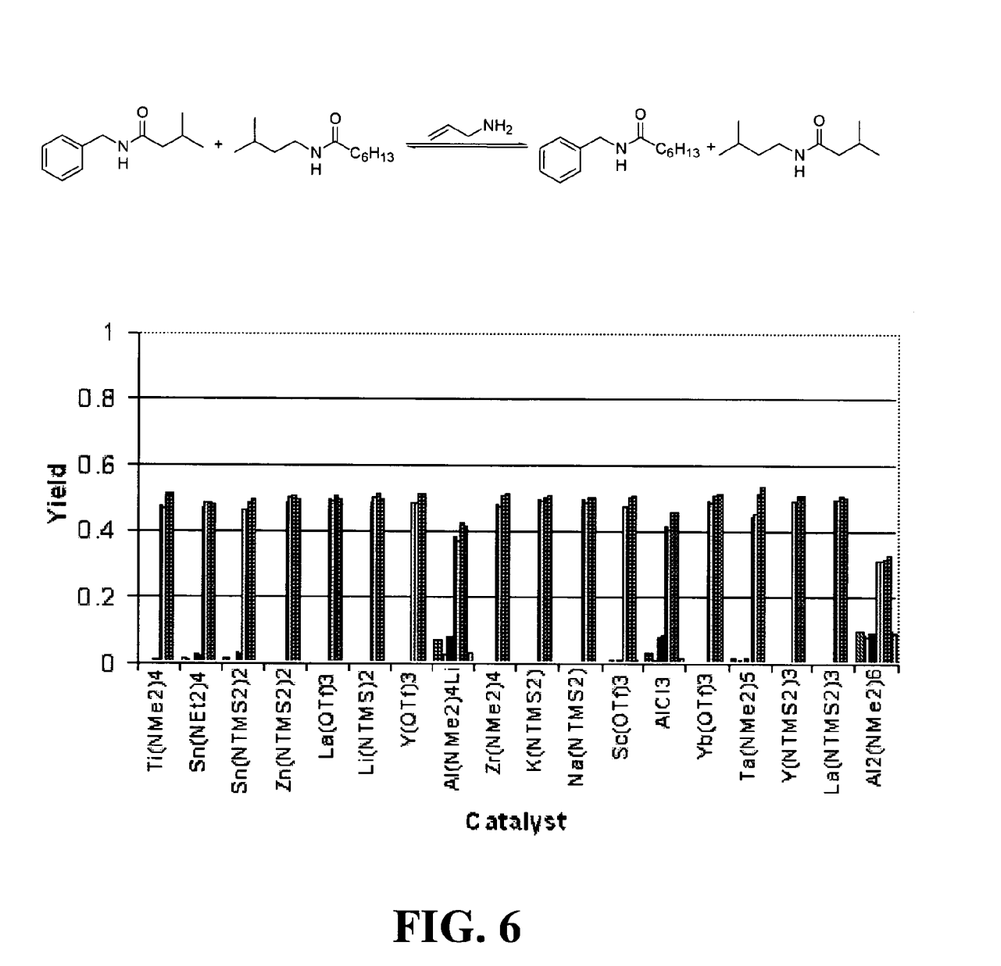
FIG. 6 shows preliminary data from the amide metathesis reactions in which $Al_2(NMe_2)_6$ is the most promising catalyst. Six reactions were run, in duplicate, for a total of 12 recorded results for each catalyst. Moving from left to right in each entry in FIG. 6, the results are presented for the following amides (in duplicate) AIA=Allyl isovaleric amide. IIA=Isoamyl isovaleric amide. AHA=Allyl heptyl amide. IHA=Isoamyl heptyl amide. BIA=Benzyl isovaleric amide. BHA=Benzyl heptyl amide.

The exchange reaction between or among amides is known as amide metathesis. The metal catalysts listed in Example 1 were also screened for this reaction. The results show that several of these metal catasyts can effect the desired transformation. The aluminum-amido complex $Al_2(NMe_2)_6$, when paired with an amine initiator, showed the best results. Results are shown (in duplicate) in FIG. 6. Moving from left to right in each entry in FIG. 6, the results are presented for the following amides (in duplicate) AIA=Allyl isovaleric amide. IIA=Isoamyl isovaleric amide. AHA=Allyl heptyl amide. IHA=Isoamyl heptyl amide. BIA=Benzyl isovaleric amide. BHA=Benzyl heptyl amide. The results for $Al_2(NMe_2)_6$ are presented in the far right-hand entry in FIG. 6. As can be seen from this entry, $Al_2(NMe_2)_6$ catalyzed the reaction of all of allyl isovaleric amide, isoamyl isovaleric amide, allyl heptyl amide, isoamyl heptyl amide, benzyl isovaleric amide, and benzyl heptyl amide Other embodiments and uses of the invention will be apparent to those skilled in the art from consideration of the specification and practice of the invention disclosed herein. All references cited herein for any reason, including all U.S. and foreign patents and patent applications, are specifically and entirely incorporated herein by reference.

It is understood that the invention is not confined to the particular construction and arrangement of parts, reagents, etc., herein illustrated and described, but embraces such modified forms thereof as come within the scope of the following claims.

What is claimed is:

1. Amide metathesis and transamidation reactions comprising reacting in an aromatic, aprotic solvent at least two reactants, the reactants comprising at least two distinct amides, or at least one amide and at least one amine, in the presence of a metal-containing catalyst, at a temperature of about 250° C. or less, wherein a reaction takes place and the reaction is selected from the group consisting of transamidation and amide metathesis reactions, and wherein the catalyst is present in the reaction in a catalyst-to-reactant molar ratio of about 0.10 or less.

2. The reaction of claim 1, wherein the reactants are reacted at a temperature of about 150° C. or less.

3. The reaction of claim 1, wherein the reactants are reacted at a temperature of from about 90° C. to about 150° C.

4. The reaction of claim 1, wherein the reactants are reacted at a temperature of from about 90° C. to about 250° C.

5. The reaction of claim 1, wherein the metal-containing catalyst is selected from the group consisting of amido-ligated transition or main group metals, transition metals bearing anionic ligands, main group metals bearing anionic ligands, Lewis acidic metal complexes, and combinations thereof.

6. The reaction of claim 1, wherein the reactants are reacted in an aromatic, non-polar, aprotic solvent.

7. The reaction of claim 1, wherein the reactants are reacted in a solvent selected from the group consisting of benzene and mono-, di-, and tri-alkyl-substituted benzenes.

8. The reaction of claim 1, wherein the reactants are reacted in toluene.

9. The reaction of claim 1, wherein the metal-containing catalyst is selected from the group consisting of: $Sc(OTf)_3$, $Ti(NMe_2)_4$ and $Al_2(NMe_2)_6$.

10. A method of synthesizing oligo- or polyamides comprising reacting amine-amide reactant combinations in an aromatic, aprotic solvent, in the presence of an aluminum-, lanthanum-, scandium-, tantalum-, tin-, titanium-, ytterbium-yttrium-, or zirconium-containing catalyst, at a temperature of from about 90° C. to about 250° C., wherein a transamidation reaction takes place, and wherein the catalyst is present in a catalyst-to-reactant molar ratio of about 0.10 or less.

11. An amide metathesis reaction comprising reacting in an aromatic, aprotic solvent two distinct amide-containing molecules, in the presence of a metal-containing catalyst, at a temperature of about 250° C. or less, wherein an amide metathesis reaction takes place, and wherein the catalyst is present in the reaction in a catalyst-to-reactant molar ratio of about 0.10 or less.

12. The reaction of claim 11, wherein the amide-containing molecules are reacted in an aromatic, non-polar, aprotic solvent.

13. The reaction of claim 11, wherein the metal-containing catalyst is selected from the group consisting of: $Sc(OTf)_3$, $Ti(NMe_2)_4$ and $Al_2(NMe_2)_6$.

14. The reaction of claim 11, wherein the metal-containing catalyst is selected from the group consisting of aluminum-, lanthanum-, scandium-, tantalum-, tin-, titanium-, ytterbium-yttrium-, and zirconium-containing catalysts, and the amide-containing molecules are reacted at a temperature of from about 90° C. to about 250° C.

15. A transamidation reaction comprising reacting in an aromatic, aprotic solvent at least one amide with at least one amine, in the presence of a metal-containing catalyst, at a temperature of about 250° C. or less, wherein a transamidation reaction takes place, and wherein the catalyst is present in the reaction in a catalyst-to-reactant molar ratio of about 0.10 or less.

16. The reaction of claim 15, wherein the amide and the amine are reacted in an aromatic, non-polar, aprotic solvent.

17. The reaction of claim 15, wherein the metal-containing catalyst is selected from the group consisting of: $Sc(OTf)_3$, $Ti(NMe_2)_4$ and $Al_2(NMe_2)_6$.

18. The reaction of claim 15, wherein the metal-containing catalyst is selected from the group consisting of aluminum-, lanthanum-, scandium-, tantalum-, tin-, titanium-, ytterbium-yttrium-, and zirconium-containing catalysts, and the amide-containing molecules are reacted at a temperature of from about 90° C to about 250° C.

* * * * *